US00PP31933P3

(12) United States Plant Patent
Neumüller

(10) Patent No.: US PP31,933 P3
(45) Date of Patent: Jul. 7, 2020

(54) APPLE TREE NAMED 'BAY 4029'

(50) Latin Name: *Malus domestica*
Varietal Denomination: Bay 4029

(71) Applicant: Michael Neumüller, Hallbergmoos (DE)

(72) Inventor: Michael Neumüller, Hallbergmoos (DE)

(73) Assignee: Michael Neumüller, Hallbergmoos (DE)

( * ) Notice: Subject to any disclaimer, the term of this patent is extended or adjusted under 35 U.S.C. 154(b) by 0 days.

(21) Appl. No.: 16/350,365

(22) Filed: Nov. 8, 2018

(65) Prior Publication Data

US 2019/0141871 P1 May 9, 2019

Related U.S. Application Data

(60) Provisional application No. 62/707,577, filed on Nov. 8, 2017.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

(56) References Cited

PUBLICATIONS

UPOV hit on an apple tree named 'Bay 4029', DE PBR APF 00762, filed Sep. 1, 2016.*

* cited by examiner

*Primary Examiner* — Anne Marie Grunberg
(74) *Attorney, Agent, or Firm* — The Webb Law Firm

(57) ABSTRACT

A new and distinct *Malus domestica* variety that bears fruits having a red skin color and good eating and keeping qualities.

5 Drawing Sheets

Botanical classification: *Malus domestica.*
Varietal denomination: 'Bay 4029'.

BACKGROUND OF THE INVENTION

The present invention comprises a new and distinct variety of apple tree, botanically known as *Malus domestica*, and referred to by the varietal name 'Bay 4029'.

The new variety is the result of a planned breeding program conducted by the inventor in Hallbergmoos, Germany. The new variety is the result of a cross between 'Rubinette' (female parent, unpatented) and 'Pomona' (male parent, unpatented). 'Bay 4029' was first asexually reproduced in Hallbergmoos, Germany via table grafting on M9 rootstock. The new variety is similar to 'Rubinette' in having highly aromatic fruits with a red skin color, but the fruits of 'Bay 4029' have firmer flesh and a longer storage time when compared to the fruits of 'Rubinette'. The long storage time of the fruits of 'Bay 4029' is similar to 'Pomona', but the fruits of 'Bay 4029' have a red skin color versus the yellow-green and red skin color of the fruits of 'Pomona'. Further, 'Bay 4029' differs from apple variety named 'Royal Gala Mitschgla' (unpatented) in exhibiting a deep purple/red fruit skin color compared to the red fruit skin color of 'Royal Gala Mitschgla'.

The following characteristics also distinguish the new variety from other varieties known to the inventor:

Striking red fruit color;
Firm and juicy fruits;
Long storage life;
Highly aromatic fruits with a hint of mango;

Late harvest time;
Little to no tendency for alternation; and
Simple and uncomplicated tree.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as possible with color illustrations of this type. It should be noted that colors may vary with growing conditions and time of year.

DESCRIPTION OF THE PLANT

Figure 1:
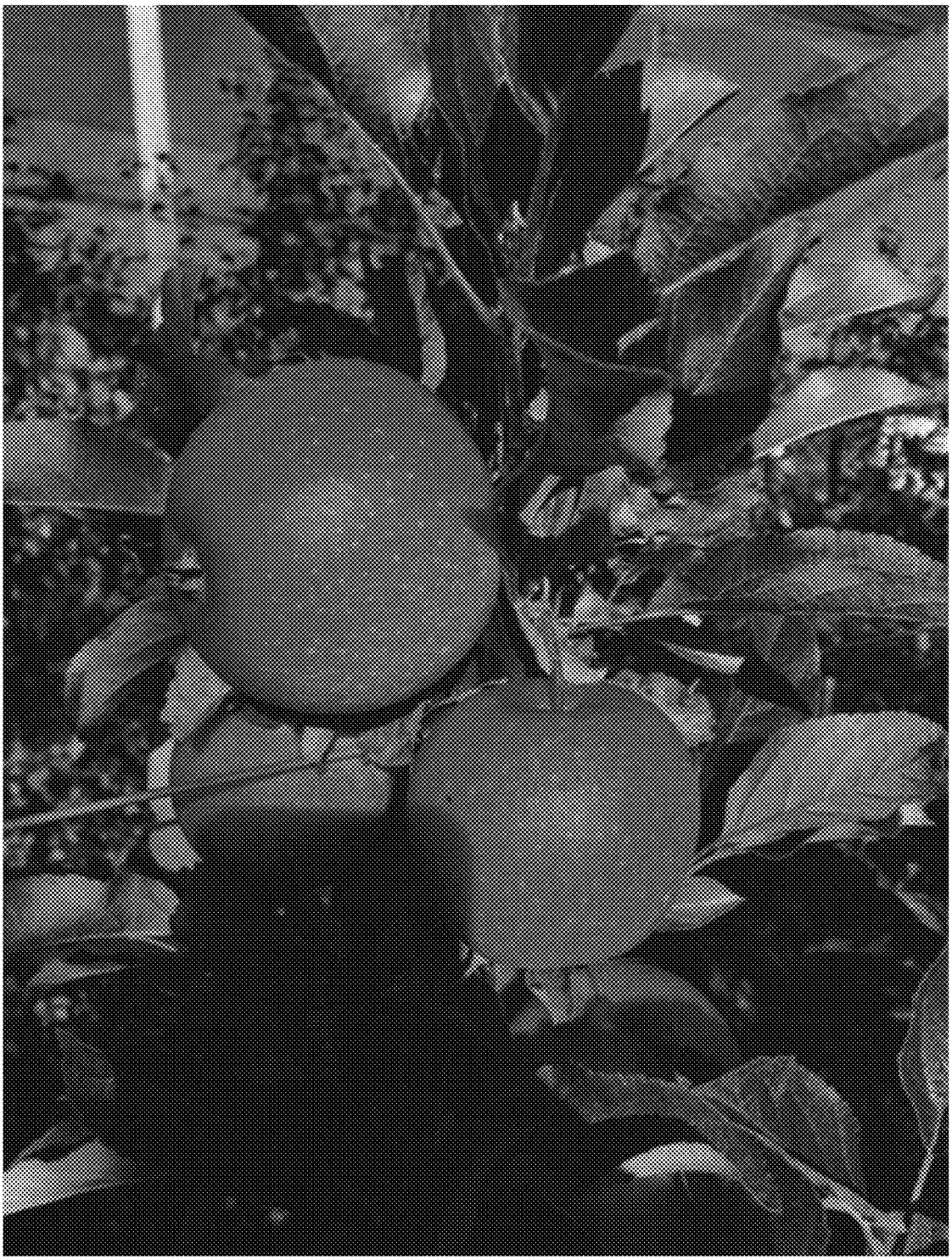
FIG. 1 illustrates a close-up view of the mature fruit of the new variety at approximately 4.5 years of age.
Figure 2:
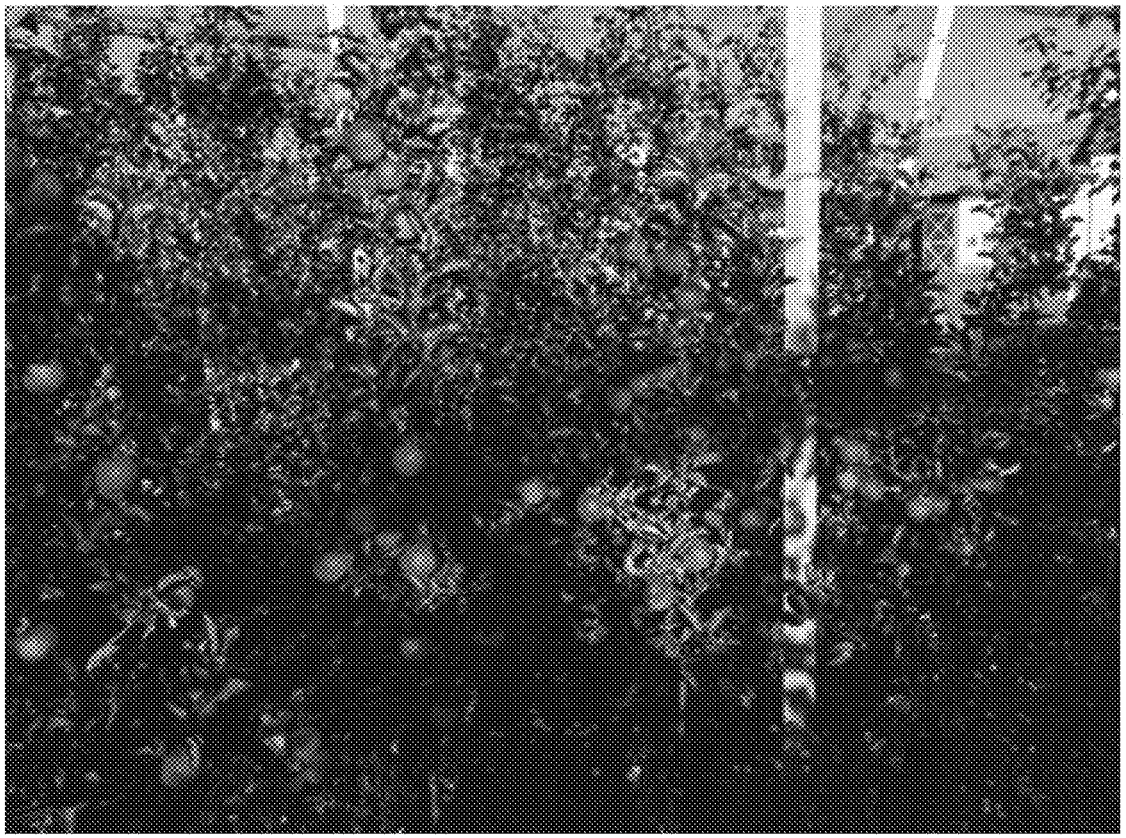
FIG. 2 illustrates multiple trees of the new variety at approximately 4.5 years of age.
Figure 3:
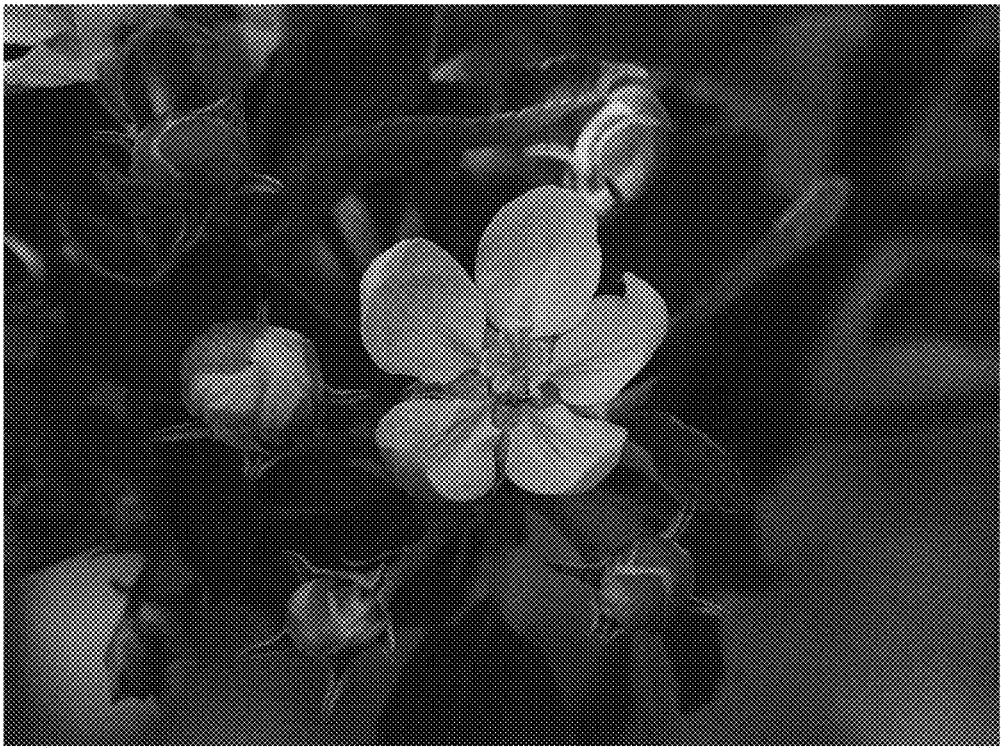
FIG. 3 illustrates flowers of the new variety at approximately 4 years of age.
Figure 4:
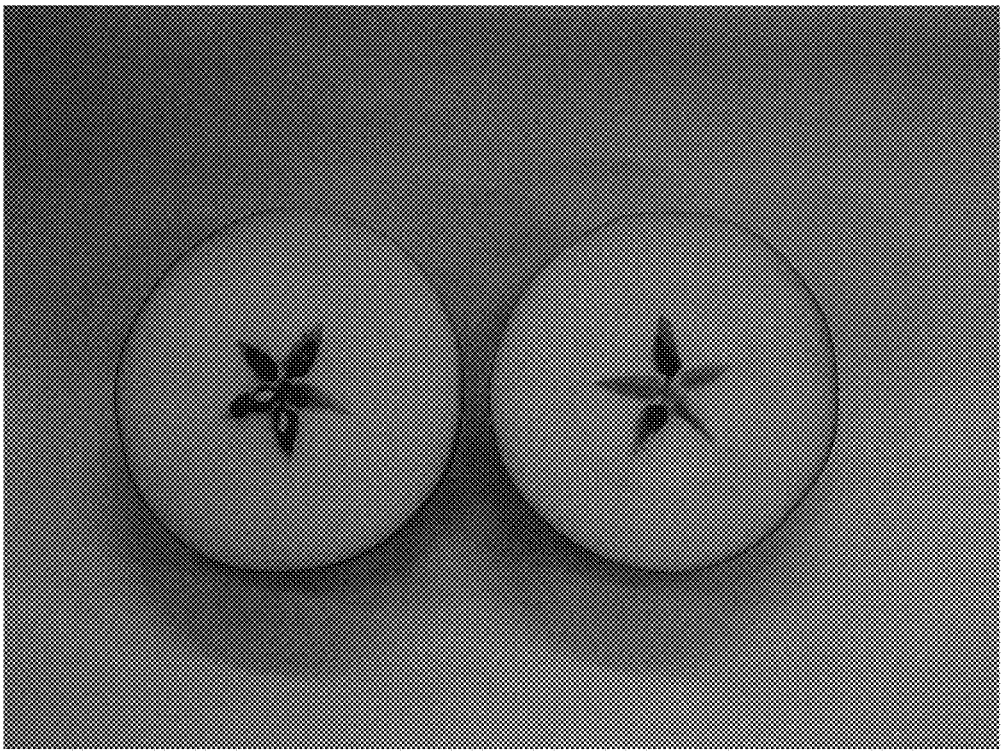
FIG. 4 illustrates a fruit of the new variety cut transversely at approximately 4.5 years of age.
Figure 5:
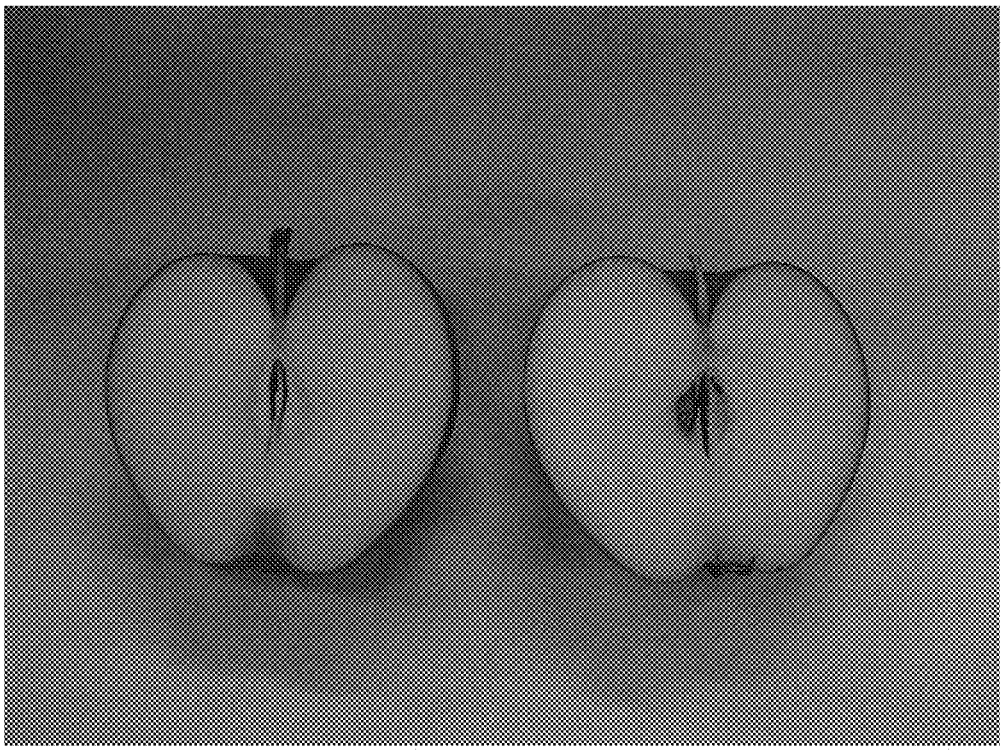
FIG. 5 illustrates a fruit of the new variety cut vertically at approximately 4.5 years of age.

The following detailed description sets forth characteristics of the new cultivar. The new variety was grown under natural field conditions in Hallbergmoos, Germany. Color references are primarily to The 2005 R.H.S. Colour Chart of The Royal Horticultural Society of London and were identified under natural light.

TREE

Age: 6 years from grafting.
Vigor: Moderate.
Branching: Freely.
Form: Ramified.
Production: Highly productive and regular with little to no alternance.
Growth type: Upright and slightly spreading.
Bearing: Annual, with thinning required.
Trunk diameter: 51 mm in diameter at 30 cm above the soil line.
Branch bark color: RHS 187A.
One-year old shoots:
*Thickness*.—5-9.5 mm.
*Growth pattern*.—Straight.
*Color*.—RHS 200C.
*Internode length*.—14-20 mm.
*Lenticels*.—Average number: 12 per cm of shoot length Length: 0.4-2.4 mm. Width: 0.3-0.7 mm. Color: RHS 155A.
Leaf blade:
*Attitude*.—Upwards and outwards in relation to shoot.
*Length*.—72 mm.
*Width*.—39 mm.
*Shape*.—Oval.
*Color*.—RHS 136A.
*Upper surface texture*.—Very slight pubescence present.
*Lower surface texture*.—Strong pubescence present.
Flowers:
*Bloom timing*.—End of April in Hallbergmoos, Germany.
*Inflorescence type*.—Umbel.
*Shape*.—Shallow cup.
*Diameter*.—39-43 mm.
*Fragrance*.—Strong.
*Fertilization*.—Diploid pollination and pollinator is required.
*Stigma position*.—Slightly above anthers.
*Pollen amount*.—Abundant.
*Petals*.—Number per flower: 5. Arrangement: Free, with slight overlapping present. Shape: Ovate. Apex: Rounded. Base: Acute. Margin: Entire. Texture: Smooth. Upper surface color: RHS 58B and RHS N155B. Lower surface color: RHS N57C and RHS N155B. Vein prominence: Medium. Vein color: RHS 61C.
*Sepals*.—Number per flower: 5. Length: 8-11 mm. Width: 4-5 mm at sepal union.
Fruit:
*Timing to maturity*.—Late — similar to 'Braeburn' (unpatented) or shortly thereafter. Approximately mid to late October in Hallbergmoos, Germany.
*Bearing type*.—On spurs and long shoots.
*General size*.—Medium.
*Shape*.—Ovoid — globose.
*Height*.—67 mm.
*Diameter*.—74 mm.
*Skin color*.—RHS 53A, with RHS 18C lenticels.
*Skin bloom*.—Weak.
*Pattern of overcolor*.—Solid flush with strongly defined strips.
*Relative area of overcolor*.—Large — 70% and RHS 53A.
*Intensity of overcolor*.—Dark.
*Ground color*.—RHS 16C.
*Area of russet*.—Around stalk attachment of fruit: Small. Around the eye basin of fruit: Absent to small.
*Ribbing*.—Nearly absent.
*Greasiness*.—Absent.
*Sepal length*.—5.5-6.5 mm.
*Stalk*.—Length: 15-25 mm. Thickness: Medium. Cavity depth: 15 mm. Cavity diameter: 25.5 mm.
*Eye basin*.—Depth: 7 mm. Width: 22.4 mm.
*Seeds*.—Length: 10.2 mm. Width: 4.5 mm. Color: RHS 200C.
*Flesh color*.—RHS 8C.
*Flesh firmness*.—High (9.5 kg/cm$^2$).
*Acidity*.—Low (3.5-5.3 g/l).
*Soluble dry matter*.—High (14-17% Brix).
*Flavor*.—Highly aromatic with a hint of mango.
Keeping quality: Extremely high. At temperatures of 1.5-2° C., apples are durable until June. In warehouse conditions, apples can be stored until September of the following year from picking.
Disease resistance: Moderate vulnerability to scab (similar to 'Elstar', U.S. Plant Pat. No. 6,450).

I claim:

1. A new and distinct variety of *Malus domestica* apple tree plant substantially as is herein described and illustrated.

* * * * *